US012326218B2

(12) United States Patent
Bouchard et al.

(10) Patent No.: US 12,326,218 B2
(45) Date of Patent: Jun. 10, 2025

(54) COUPLING DEVICE AND BASE MEMBER FOR COUPLING DEVICE

(71) Applicant: TECHNOLOGIES CGC INC., Quebec (CA)

(72) Inventors: Carl Bouchard, Quebec (CA); Tommy Lapierre, Quebec (CA); Bruno Desaulniers, Quebec (CA)

(73) Assignee: TECHNOLOGIES CGC INC., Quebec (CA)

( * ) Notice: Subject to any disclaimer, the term of this patent is extended or adjusted under 35 U.S.C. 154(b) by 34 days.

(21) Appl. No.: 18/316,571

(22) Filed: May 12, 2023

(65) Prior Publication Data

US 2023/0366505 A1    Nov. 16, 2023

Related U.S. Application Data

(60) Provisional application No. 63/341,657, filed on May 13, 2022.

(51) Int. Cl.
*F16M 13/02* (2006.01)

(52) U.S. Cl.
CPC ......... *F16M 13/02* (2013.01); *F16M 2200/02* (2013.01)

(58) Field of Classification Search
CPC ... F16M 13/02; F16M 13/022; F16M 2200/02
USPC ............ 248/346.01, 346.03, 346.04, 346.06, 248/222.11, 222.12, 222.13, 222.51
See application file for complete search history.

(56) References Cited

U.S. PATENT DOCUMENTS

| 4,511,158 | A | | 4/1985 | Varga et al. |
| 5,152,486 | A | | 10/1992 | Kabanek et al. |
| 5,325,263 | A | * | 6/1994 | Singer ................ H01R 13/6315 439/157 |
| 5,362,021 | A | | 11/1994 | Phillips |
| 6,625,014 | B1 | * | 9/2003 | Tucker .................... G06F 1/184 361/679.33 |

(Continued)

FOREIGN PATENT DOCUMENTS

| DE | 102017110001 A1 | 11/2018 |
| WO | 2021168586 A1 | 9/2021 |

OTHER PUBLICATIONS

European Search Report issued in co-pending European patent applicatio No. 23173194.4 on Oct. 12, 2023.

*Primary Examiner* — Alfred J Wujciak
(74) *Attorney, Agent, or Firm* — BCF LLP (57) ABSTRACT

A coupling device includes base and plate members that are connectable to one another. The base member has a body with a coupling face, a stopper connected to the body and moveable between neutral and locked positions, and an actuation mechanism for moving the stopper. In a connected mode of the coupling device, a contact portion of the coupling face contacts a contact face of the plate member, and an alignment area of the contact portion corresponds to a position of an opening of the plate member. In the neutral position, the stopper is aligned with the alignment area and can be received in the opening thereby permitting removal of the plate member from the base member. In the locked position, the stopper is misaligned with the alignment area, and extends over a part of the plate member to restrict movement of the plate member away from the base member.

13 Claims, 11 Drawing Sheets

(56) References Cited

U.S. PATENT DOCUMENTS

| | | | |
|---|---|---|---|
| 7,175,152 B2* | 2/2007 | Dittmer | F16M 13/02 248/222.51 |
| 7,891,621 B1 | 2/2011 | Secora et al. | |
| 8,011,071 B2* | 9/2011 | O'Brien | A61M 16/1075 248/221.11 |
| 9,746,125 B2 | 8/2017 | Bowman | |
| 10,732,680 B1* | 8/2020 | Lu | G11B 33/128 |
| 11,007,951 B1 | 5/2021 | Zarecky | |
| 2002/0011543 A1 | 1/2002 | Chinn et al. | |
| 2003/0046764 A1 | 3/2003 | Smeed | |
| 2008/0217910 A1 | 9/2008 | Walke | |
| 2012/0087084 A1* | 4/2012 | Nguyen | G06F 1/187 361/679.37 |
| 2012/0262039 A1 | 10/2012 | Daugbjerg et al. | |
| 2013/0037676 A1* | 2/2013 | Guo | G06F 1/187 248/310 |
| 2014/0374564 A1 | 12/2014 | Schroeder et al. | |
| 2014/0374565 A1 | 12/2014 | Tan | |
| 2015/0041419 A1 | 2/2015 | Hasegawa | |
| 2015/0090849 A1 | 4/2015 | Breitweiser et al. | |
| 2015/0273138 A1 | 10/2015 | Wolff et al. | |
| 2016/0031382 A1 | 2/2016 | Chinn et al. | |
| 2016/0073537 A1* | 3/2016 | Tseng | G06F 1/183 361/809 |
| 2016/0324701 A1 | 11/2016 | Cambridge et al. | |
| 2017/0209318 A1 | 7/2017 | Schroeder et al. | |
| 2019/0045651 A1* | 2/2019 | Ehlen | E05B 65/006 |
| 2022/0107052 A1 | 4/2022 | Tsorng et al. | |

* cited by examiner

FIGURE 11

COUPLING DEVICE AND BASE MEMBER FOR COUPLING DEVICE

CROSS-REFERENCE TO RELATED APPLICATIONS

This application claims the benefit of U.S. Provisional patent application Ser. No. 63/341,657, filed on May 13, 2022. The contents of the aforementioned application is incorporated by reference herein.

TECHNICAL FIELD

The present technology relates to coupling devices, such as, but not limited to, coupling devices which include a base member and a plate member. The present technology also relates to base members for coupling devices.

BACKGROUND

Coupling devices for mounting devices to a support structure, where the coupling devices have a member to which the device can be attached and another member which can be attached to the support structure are known.

In such known coupling devices, achieving the connection and/or disconnection between the two members can be difficult and/or time consuming, for example requiring specific relative positioning therebetween. Then, once connected to one another, the two members could be fixed to one another, thereby not allowing adjustment of a position of the device that is mounted to the coupling device.

Additionally, known coupling devices can be complex with many components and therefore do not readily lend themselves to use in a medical environment in which cleaning or sterilization of the fixing system may be required.

Furthermore, in a variety of industries such as the medical industry, items are made to be mobile so as to be transported from one location to another. In the case of the medical industry, this could be to move an item from one patient to another. There is a desire for a coupling device that can secure an item to a support surface during transportation and/or upon reaching a location.

Therefore, there is a desire for a coupling device that can overcome at least some of the above-described drawbacks.

SUMMARY

It is an object of the present technology to ameliorate at least some of the inconveniences present in the prior art.

According to one aspect of the present technology, there is provided a coupling device including a base member and a plate member which are configured to be releasably connectable to one another. The base member has a body, a stopper and an actuation mechanism. The body has a coupling face having a contact portion for contacting a contact face of the plate member in a connected mode of the coupling device. The contact portion includes an alignment area which corresponds to a position of an opening of the plate member when the coupling device is in the connected mode. The stopper is operatively connected to the body, extends from the coupling face and is positioned in the contact portion. The stopper is sized and shaped to be received in the opening of the plate member. The stopper is moveable between a neutral position and a locked position. In the neutral position, the stopper is aligned with the alignment area and can be received in the opening of the plate member when the coupling device is in the connected mode. The neutral position of the stopper permits removal of the plate member from the base member. In the locked position, the stopper is misaligned with the alignment area, and when the contact face of the plate member contacts the contact area with the stopper received in the opening, the stopper extends over a part of the plate member to restrict movement of the plate member away from the base member. The actuation mechanism is for selectively moving the stopper between the neutral and locked positions.

In some embodiments, in the neutral position, a central axis of the stopper is aligned with the central axis of the alignment area of the contact portion.

In some embodiments, the stopper is connected to the actuation mechanism by a neck extending away from the coupling face, a thickness of the stopper being greater than a thickness of the neck.

In some embodiments, the stopper is asymmetrically attached to the neck such that a central axis of the neck is misaligned with a central axis of the stopper.

In some embodiments, the actuation mechanism is configured to rotate the neck about the central axis of the neck, the rotation of the neck causing the movement of the stopper between the neutral and locked positions.

In some embodiments, the movement of the stopper between the neutral and locked positions defines an arcuate path.

In some embodiments, the actuation mechanism comprises an actuator connected to the neck by one or more gears, for effecting rotation of the neck on actuation of the actuator.

In some embodiments, the actuator is a lever.

In some embodiments, the coupling device further includes a guide member on the base member, the lever being configured to slide along the guide member.

In some embodiments, the one or more gears includes a first gear, which is a gear wheel, extending around, and attached to, the neck, as well as a second gear pivotally connected to the body of the base member about a pivot point, the second gear having a first portion attached to the actuator and a second portion engaged with the first gear wheel, and the second gear pivoting on actuation of the actuator.

In some embodiments, the stopper is spaced from the coupling face, thereby defining a gap sized to accommodate a thickness of the plate member.

In some embodiments, the coupling device further includes at least one positioning member on the coupling face of the base member for defining at least a portion of a perimeter of the contact portion and delimiting a movement of the plate member along the coupling face.

In some embodiments, the at least one positioning member comprises at least one protrusion extending from the contact portion.

In some embodiments, the coupling device further includes a lock for locking the actuation mechanism in one of the neutral and locked positions.

According to another aspect of the present technology, there is provided a base member of a coupling device, which includes the base member and a plate member. The base and plate members are configured to be releasably connectable to one another. The base member has a body, a stopper and an actuation mechanism. The body has a coupling face which has a contact portion for contacting a contact face of the plate member in a connected mode of the coupling device. The contact portion includes an alignment area which corresponds to a position of an opening of the plate member when the coupling device is in the connected mode. The stopper extends from the coupling face and positioned in the contact portion. The stopper is sized and shaped to be received in the opening of the plate member. The stopper is moveable between a neutral position and a locked position. In the neutral position, the stopper is aligned with the alignment area and can be received in the opening of the plate member when the coupling device is in the connected mode. The neutral position of the stopper permits removal of the plate member from the base member. In the locked position, the stopper is misaligned with the alignment area, and when the contact face of the plate member contacts the contact area with the stopper received in the opening, the stopper extends over a part of the plate member to restrict movement of the plate member away from the base member. The actuation mechanism is for moving the stopper between the neutral and locked positions.

In some embodiments, in the neutral position, a central axis of the stopper is aligned with a central axis of the alignment area of the contact portion.

In some embodiments, the stopper is connected to the actuation mechanism by a neck extending away from the coupling face, a thickness of the stopper being greater than a thickness of the neck.

In some embodiments, the stopper is asymmetrically attached to the neck such that a central axis of the neck is misaligned with a central axis of the stopper.

In some embodiments, the actuation mechanism is configured to rotate the neck about the central axis of the neck, the rotation of the neck causing the movement of the stopper between the neutral and locked positions.

In some embodiments, the movement of the stopper between the neutral and locked positions defines an arcuate path.

In some embodiments, the actuation mechanism comprises an actuator connected to the neck by one or more gears, for effecting rotation of the neck on actuation of the actuator.

In some embodiments, the actuator is a lever.

In some embodiments, the coupling device further includes a guide member on the base member, the lever being configured to slide along the guide member.

In some embodiments, the one or more gears include a first gear and a second gear. The first gear, which is a gear wheel, extends around, and is attached to, the neck. The second gear is pivotally connected to the body of the base member about a pivot point. The second gear has a first portion attached to the actuator and a second portion engaged with the first gear wheel. The second gear pivots on actuation of the actuator.

In some embodiments, the stopper is spaced from the coupling face, thereby defining a gap sized to accommodate a thickness of the plate member.

In some embodiments, the coupling device further includes at least one positioning member on the coupling face of the base member for defining at least a portion of a perimeter of the contact portion and delimiting a movement of the plate member along the coupling face.

In some embodiments, the at least one positioning member comprises at least one protrusion extending from the contact portion.

Advantages

In certain embodiments, a coupling device according to embodiments of the present technology can provide quick, one hand connection and disconnection between a member connected to a connecting surface and a member connected to a device.

In certain embodiments, the coupling device, when in the connected mode, enables rotational movement between the members of the coupling device.

In certain embodiments, the coupling device can be easy to clean and disinfect. In some instances, the coupling device can be made of material resistant to chemicals used in cleaning and/or disinfecting.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

As used herein, the term "and/or" is to be taken as specific disclosure of each of the two specified features or components with or without the other. For example "A and/or B" is to be taken as specific disclosure of each of (i) A, (ii) B and (iii) A and B, just as if each is set out individually herein.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects, and advantages of implementations of the present technology will become apparent from the following description, the accompanying drawings, and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

The present disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements.

According to embodiments of the present technology, there is provided a coupling device having a base member and a plate member. The base member is connectable to a support surface, whereas the plate member is connectable to a device. The base member and the plate member can be connected to one another to connect the device to the support surface. When connected, the plate member cannot be separated from the base member in a transverse direction whilst rotational movement of the plate member relative to the base member is possible thereby permitting a change in the orientation of the device relative to the support surface.

Figure 1:
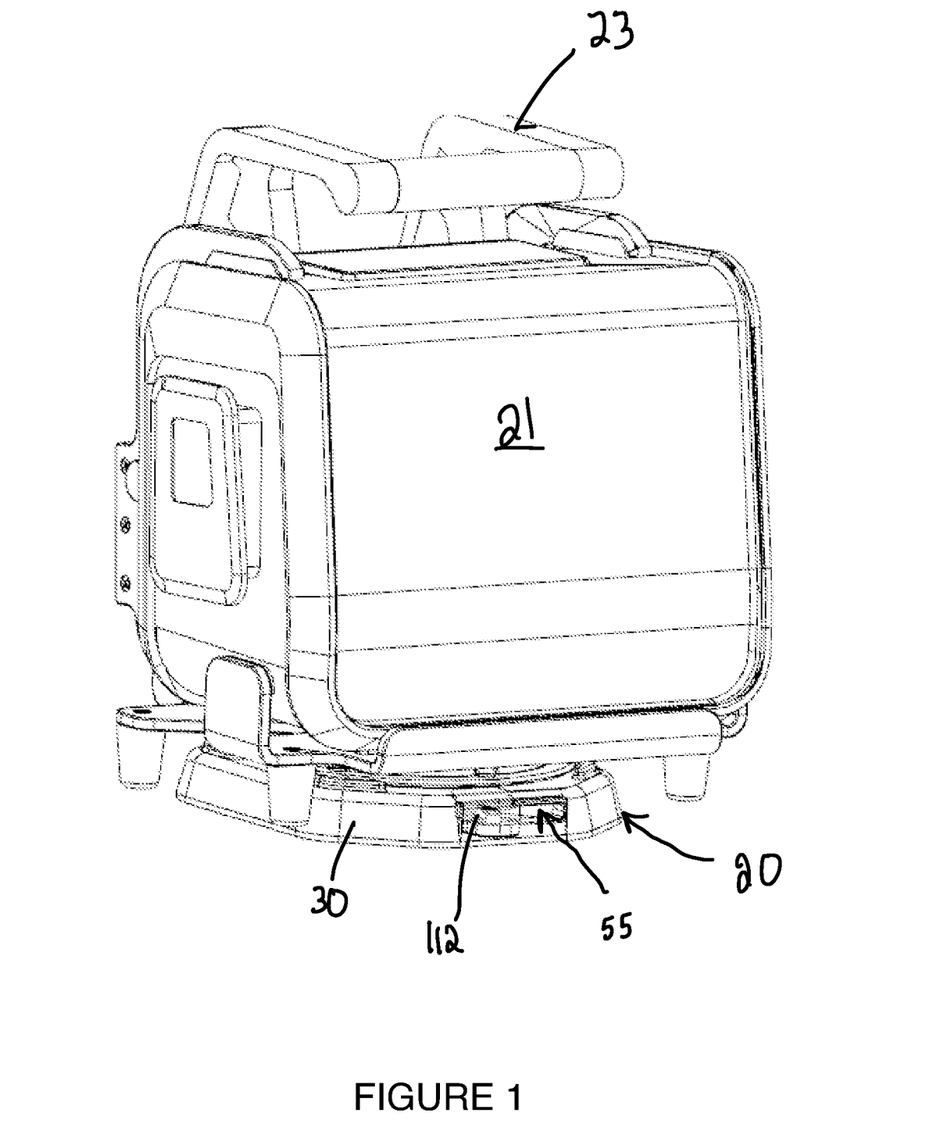
FIG. 1 is a perspective view taken from a top, front, right side of a coupling device according to an embodiment of the present technology, to which is connected a holder and a ventilator.
Figure 2:
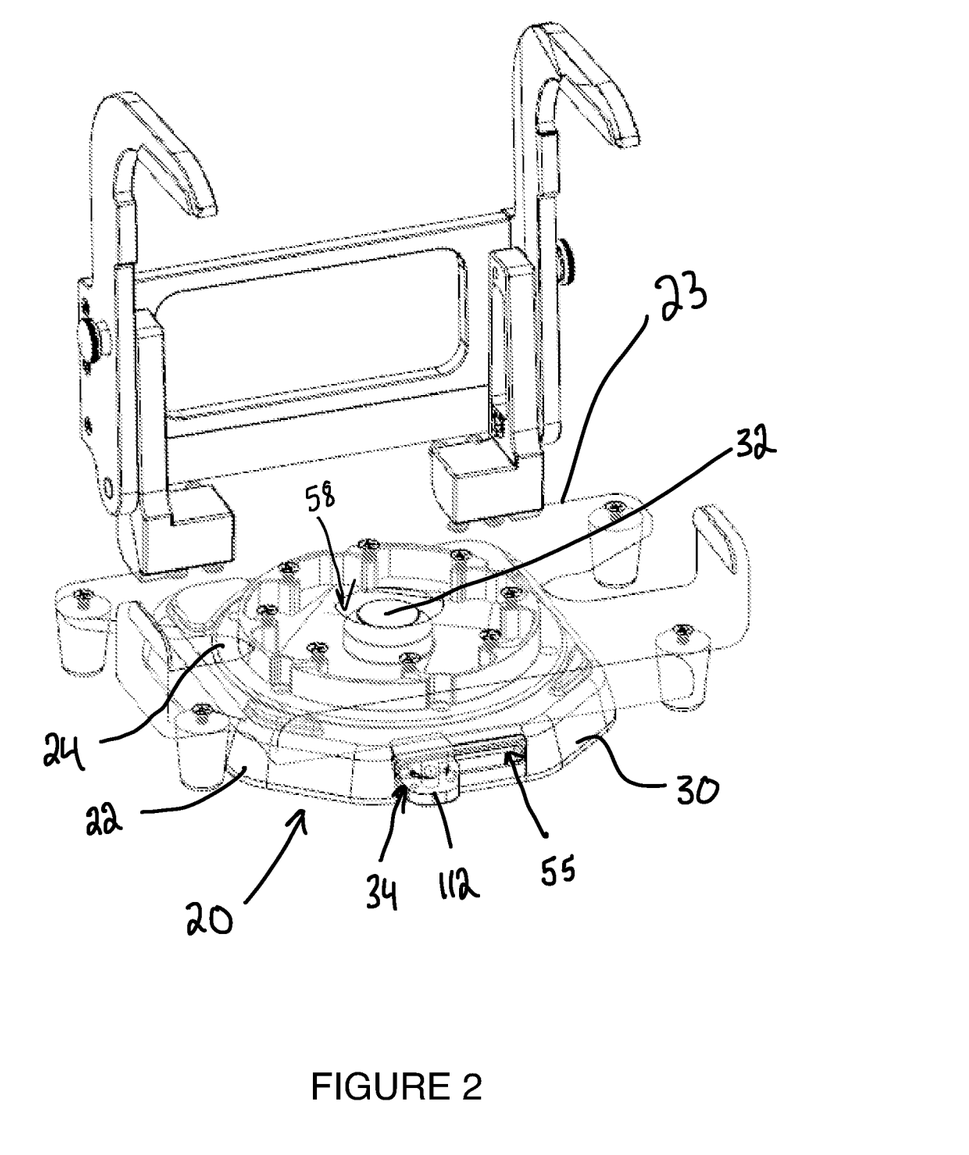
FIG. 2 is a perspective view taken from a top, front, right side of the coupling device and the holder of FIG. 1, with part of the holder being shown in transparency.

The connection of the base member and the plate member which avoids transverse separation whilst allowing relative rotation is made possible by a stopper which extends from the body and can be moved, by an actuation mechanism, relative to the body to extend over the plate member and block its transverse movement away from the base member. Referring to FIGS. 1 and 2, there is shown a coupling device 20 having connected thereto a device 21 and a holder 23. In the present embodiment, the device 21 is a ventilator, but it is understood that the device 21 could be any other type of device.

The coupling device 20 includes a base member 22 and a plate member 24. The base and plate members 22, 24 are removably connectable to one another. The base member 22 is connectable to a support surface such as a floor, a table, a cart or a shelf, and the plate member 24 is connectable to the device 22. In some embodiments, the support surface could be a vertical support surface such as a wall. The coupling device 20 is adjustable between a connected mode, in which the base and plate members 22, 24 are retained to one another (FIGS. 3 and 4), and a disconnected mode, in which the base and plate members 22, 24 are free to be separated from one another. The coupling device 20 will be described with reference to a generally horizontal support surface, such that when referring to "vertical" or "upwardly" directions, it is meant generally transversally to the support surface while the coupling device 20 is in use.

Referring to FIGS. 5 to 10, the base member 22 will first be described in greater detail. The base member 22 has a body 30, a stopper 32 and an actuation mechanism 34 which can cause the stopper 32 to move relative to the body 30.

The body 30 has a two-part construction and comprises an upper part 42 and a lower part 44. The upper and lower parts 42, 44 are selectively connectable to one another. In the present embodiment, the upper and lower parts 42, 44 are connectable via body fasteners (not shown) which are removable. It is contemplated that in other embodiments, the upper and lower parts 42, 44 could be permanently connected to one another, such as using adhesive or welding, instead of being selectively connectable.

A bottom surface of the lower part 44, which is configured to contact the support surface, is generally flat. In some embodiments, the lower part 44 could be fixedly connected to the support surface, for example via bolts or screws or adhesive. The lower part 44 defines four connecting apertures 46 at corners thereof. The connecting apertures 46 are configured to receive the body fasteners therethrough for connecting with the upper part 42. It is contemplated that in other embodiments, there could be more or less than four connecting apertures. The lower part 44 also defines four central apertures 48 for connecting with a connecting assembly 70. It is contemplated that there could be more or less than four central apertures. The central apertures 48 are counterbore apertures, so that body fasteners received therein do not interfere between the bottom surface of the lower part 44 and the supporting surface. The central apertures 48 could also be other types of apertures, such as countersunk apertures.

The upper part 42 has a coupling face 50 and a sidewall 52 that extends downwardly from a perimeter of the coupling face 50. The sidewall 52, at a bottom thereof, defines connecting apertures 54 configured to receive the body fasteners therein for connecting with the lower part 44. The connecting apertures 54 are configured to be aligned with the connecting apertures 46 when the upper and lower parts 42, 44 are connected. At a front thereof, the sidewall 52 also defines a slot 55. The body 30 also has a guide member 57 received at a bottom of the slot 55. Although in the present embodiment, the guide member 57 is connected the lower part 44 via fasteners (not shown), it is contemplated that in some embodiments, the guide member 57 could be connected to the upper part 42. In other embodiments, the guide member 57 could be integral with the upper or lower parts 42, 44. For instance, the slot 55 could be configured to define the guide member 57 within the sidewall 52. The guide member 57 has, on either lateral side thereof, stopping segments 59. As will be described below, the slot 55 is configured to receive part of the actuation mechanism 34 therein, and the guide member 57 is configured to guide part of the actuation mechanism 34. In some embodiments, a gasket (not shown) could be placed around the slot 55 to prevent entry of unwanted substances within the body 30 through slot 55.

Figure 11:
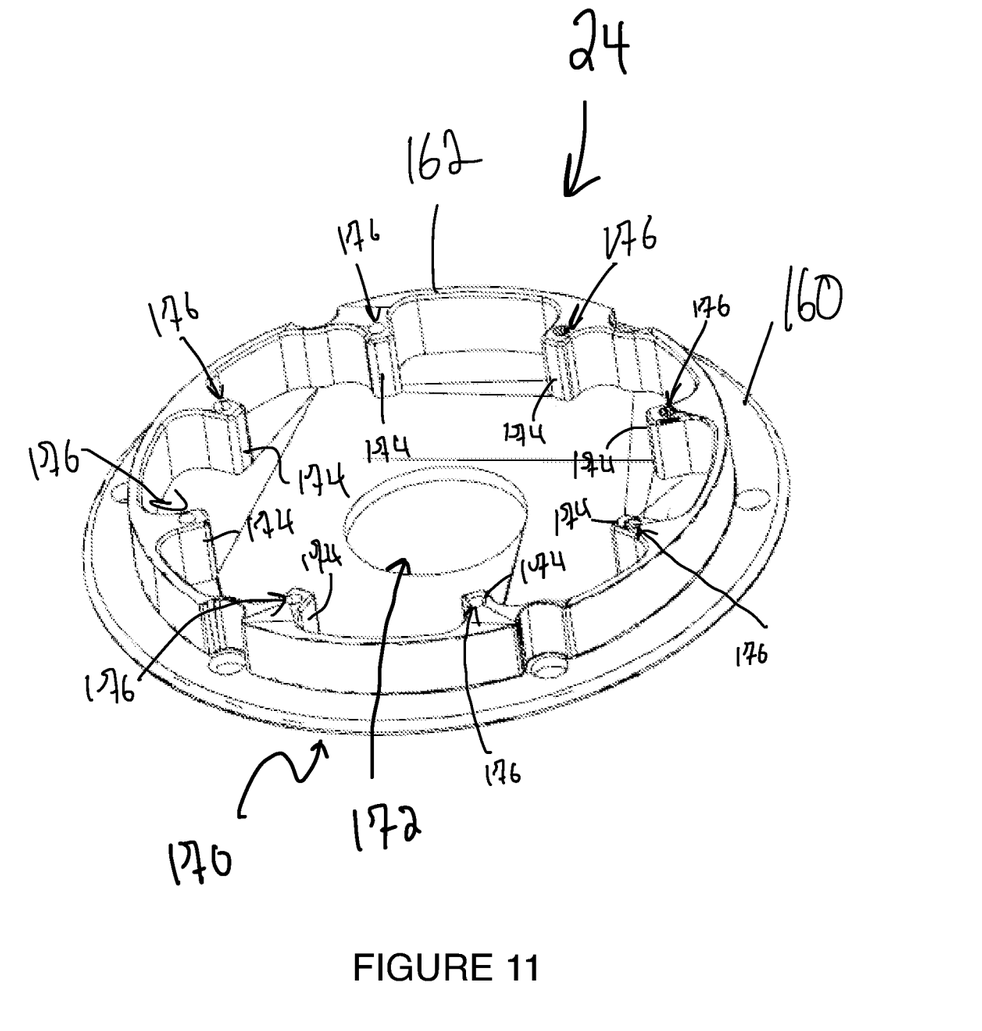
FIG. 11 is a perspective view taken from a top, front, left side of a plate member of the coupling device of FIG. 1.

The coupling face 50 has a contact portion 56 for contacting a contact face 170 of the plate member 24 (FIG. 11). The contact portion 56 also has an alignment area 58. In the present embodiment, the alignment area 58 is generally defined at a central portion of the coupling face 50. It is contemplated that in other embodiments, the alignment area 58 could be defined elsewhere along the coupling face 50. The alignment area 58 corresponds to an area where there is an alignment of respective features of the base and plate members 22, 24 to allow the base and plate members 22, 24 to connect. The respective features comprise the stopper 32 which extends from the coupling face 50 and an opening 172 of the plate member 54. Instead of an alignment area, there may be provided respective alignment points on the coupling face 50 and the plate member 24, which when they are aligned permit connection and disconnection of the base and plate members 22, 24.

The coupling face 50 also has peripheral positioning members 62 and a central positioning member 63 for positioning the plate member 24 relative to the base member 22. The peripheral positioning members 62 and/or the central positioning member 63 are optional. In the present embodiment, there are four peripheral positioning members 62 generally positioned at each corner of the coupling face 50. It is contemplated that in other embodiments, there could be more or less than four positioning members 62. Each of the positioning members 62 is a protrusion having an inner edge 64 that is complementary to a shape of a periphery of the plate member 24. Thus, being that, according to the present embodiment, the plate member 24 is circular, the inner edge 64 of each of the positioning members 62 is arcuate. The positioning members 62 also define a perimeter of the contact portion 56. The central positioning member 63 is a protrusion extending from the contact face, and is positioned to be within the alignment area 58. A central positioning member axis 65 of the central positioning member 63 is aligned with a central alignment area axis 58a of the alignment area 58.

A stopper aperture 60 (FIG. 5) is defined in the coupling face 50. Specifically, the stopper aperture 60 is defined in the central positioning member 63, and is offset from the center of the central positioning member 63 (and thus offset from the alignment point 58). It is contemplated that in some embodiments, a gasket could be added below the stopper aperture 60 to cover the stopper aperture 60, and to prevent unwanted entry of substances within the body 30 through the stopper aperture 60.

Figure 8:
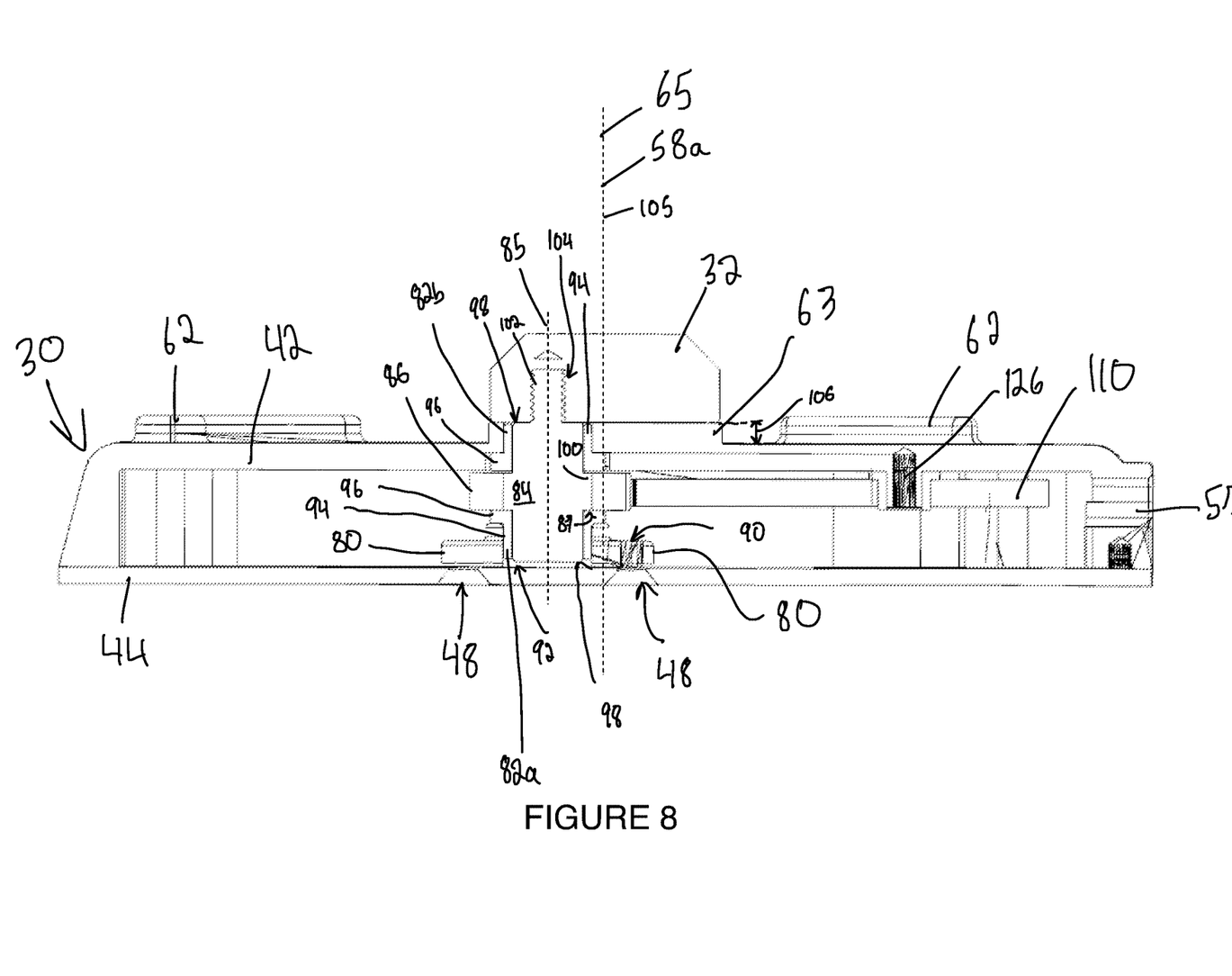
FIG. 8 is a cross-sectional view of the base member of FIG. 3 taken across a lateral center of the base member.

With reference to FIG. 8, the stopper 32, which is operatively connected to the body 30, will now be described. The stopper 32 is connected to the body 30 by the connecting assembly 70, which includes a base 80, upper and lower retainers 82a, 82b, a neck 84 and a stopper gear 86. Specifically, the connecting assembly 70 connects the stopper 32 to the body 30 while enabling the stopper 32 to rotate relative to the body 30.

The base 80 defines four base apertures 90 that are configured to be aligned with the central apertures 48 such that the connecting assembly 70 can be connected to the lower part 44 with the use of fasteners such as screws or bolts. It is contemplated that in some embodiments, the base 80 could be connected to the lower part 44 differently, such as, for example, by an adhesive. The base 80 defines a center aperture 92 that is configured to receive part of the neck 84 and part of the lower retainer 82a.

The lower and upper retainers 82a, 82b are similar, and thus, only the lower retainer 82a will be described herewith. The lower retainer 82a has a tubular body 94 that extends vertically in use (transversely to the lower part 44). At one end thereof, the lower retainer 82a has a flange 96 extending radially from the tubular body 94 direction. An aperture 98 is defined through a length of the lower retainer 82a (i.e., through the body 94 and the flange 96). As will be described below, the aperture 98 is configured to receive part of the neck 84 therein, and the flange 96 is configured to abut an intermediate portion 100 of the neck 84. The lower retainer 82a is made of a material having low friction with the base 80 and the neck 84.

The neck 84, which is configured to be partially received in the center aperture 92 of the base 80 and the aperture 98 of the upper and lower retainers 82a, 82b, extends in the vertical direction in use along a central neck axis 85. The neck 84 has the intermediate portion 100. The intermediate portion 100, which extends radially, has a hexagonal shape. It is contemplated that in other embodiments, the intermediate portion 100 could have another shape with corners, such as for example, a square. In some embodiments, the intermediate portion 100 could have another shape without corners, such as for example, an ellipse. The stopper gear 86 is connected to the neck 84 by the intermediate portion 100, and the shape of the intermediate portion 100 is complementary to an inner aperture 87 of the stopper gear 86. The shape of the intermediate portion 100 and the inner aperture 87 provide a fixed relationship between stopper gear 86 and the neck 84. In other words, the neck 84 and the stopper gear 86 are mechanically interlocked to one another. It is contemplated that in some embodiments, the neck 84 and the stopper gear 86 could be connected differently. In some instances, the neck 84 and the stopper gear 86 could be integral. The neck 84 also has, extending from a top surface thereof, a connecting portion 102. In the present embodiment, the connecting portion 102 is threaded, and is configured to be fastened to a threaded aperture 104 defined in the stopper 32. As such, the connecting portion 102 extends through the stopper aperture 60 when the connecting portion 102 is connected to the stopper 32 and the connecting assembly 70 is connected to the body 30.

The stopper gear 86, as mentioned above, is connected to the neck 84 via the intermediate portion 100. The stopper gear 86 is a gear wheel that defines the inner aperture 87 at a center thereof so as to be connectable to the neck 84. The stopper gear 86 is rotatable about the central neck axis 85 to cause a rotation of the neck 84, and thus cause a rotation of the stopper 32.

Thus, when the connecting assembly 70 is assembled and connected to the body 30, the base 80 is connected to the lower part 44 via fasteners (not shown) that extend through the central apertures 48 of the lower part 44 and the base apertures 90. The body 94 of the lower retainer 82a is received in the center aperture 92 of the base 80, and a lower surface of the flange 96 abuts an upper surface of the base 80. The neck 84 is received in the aperture 98 of the lower retainer 82a such that an upper surface of the flange 96 abuts a lower surface of the intermediate portion 100. The stopper gear 86 is connected to the intermediate portion 100. The neck 84 is also received in the aperture 98 of the upper retainer 82b. The upper retainer 82b is positioned and oriented so that a lower surface flange 96 abuts the intermediate portion 100. The flange 96 is also positioned so that an upper surface thereof can abut a lower surface of the upper part 42, below the stopper aperture 60. The connecting portion 100 extends through the stopper aperture 60.

As will be described below, a movement of the stopper 32 away from the neck 84, is delimited by the connecting assembly 70, notably due to the abutment of the flanges 96 of the upper and lower retainers 82a, 82b.

Also, the neck 84 is rotatable relative to the body 30. In the present embodiment, this rotational relationship is a result of low friction between a material of the neck 84 and a material of the retainers 82a, 82b. It is contemplated that in some embodiments, the neck 84 could be connected to bearings where outer races of the bearings would be fixedly connected to the upper and lower retainers 82a, 82b, and inner races of the bearings would be fixedly connected to the neck 84.

The stopper 32 is shaped and sized to be received through the opening 172 of the plate member 54. In the present embodiment, a perimeter of the stopper 32 and a perimeter of the opening 172 are both circular. The stopper 32 defines, at a bottom thereof, the threaded aperture 104. The threaded aperture 104 is offset from a central stopper axis 105. As such, the central stopper axis 105 is offset (i.e., misaligned) from the central neck axis 85 of the neck 84. In other words, the stopper 32 is asymmetrically attached to the neck 84.

As will be described below, the stopper 32 is moveable between a neutral position (FIGS. 3 and 5), in which the central stopper axis 105 is aligned with the alignment point 58, and a locked position (FIGS. 4 and 6), in which the central stopper axis 105 is offset from the alignment point 58, by actuation of the actuation mechanism 34. The stopper 32 is spaced from the contact portion 56 of the coupling face 50, thereby defining a gap 106 (shown in FIG. 8). In some embodiments, the stopper 32 could abut the central positioning member 63. The gap 106 is configured to accommodate a thickness of the plate member. Given the offset between the connection of the neck 84 and the stopper 32 and the central stopper axis 105, movement of the stopper 32 between the locked and neutral positions defines an arcuate path.

Figure 9:
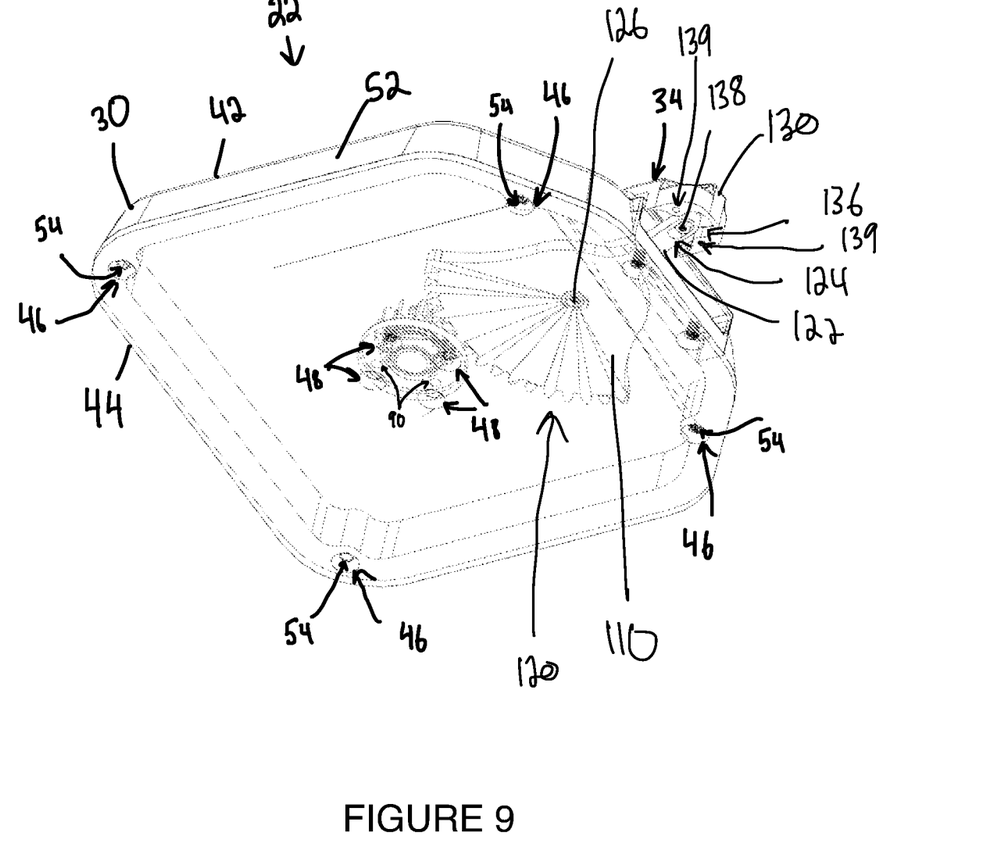
FIG. 9 is a perspective view taken from a bottom, front, right side of the base member of FIG. 3, with a lower part being shown in transparency.
Figure 10:
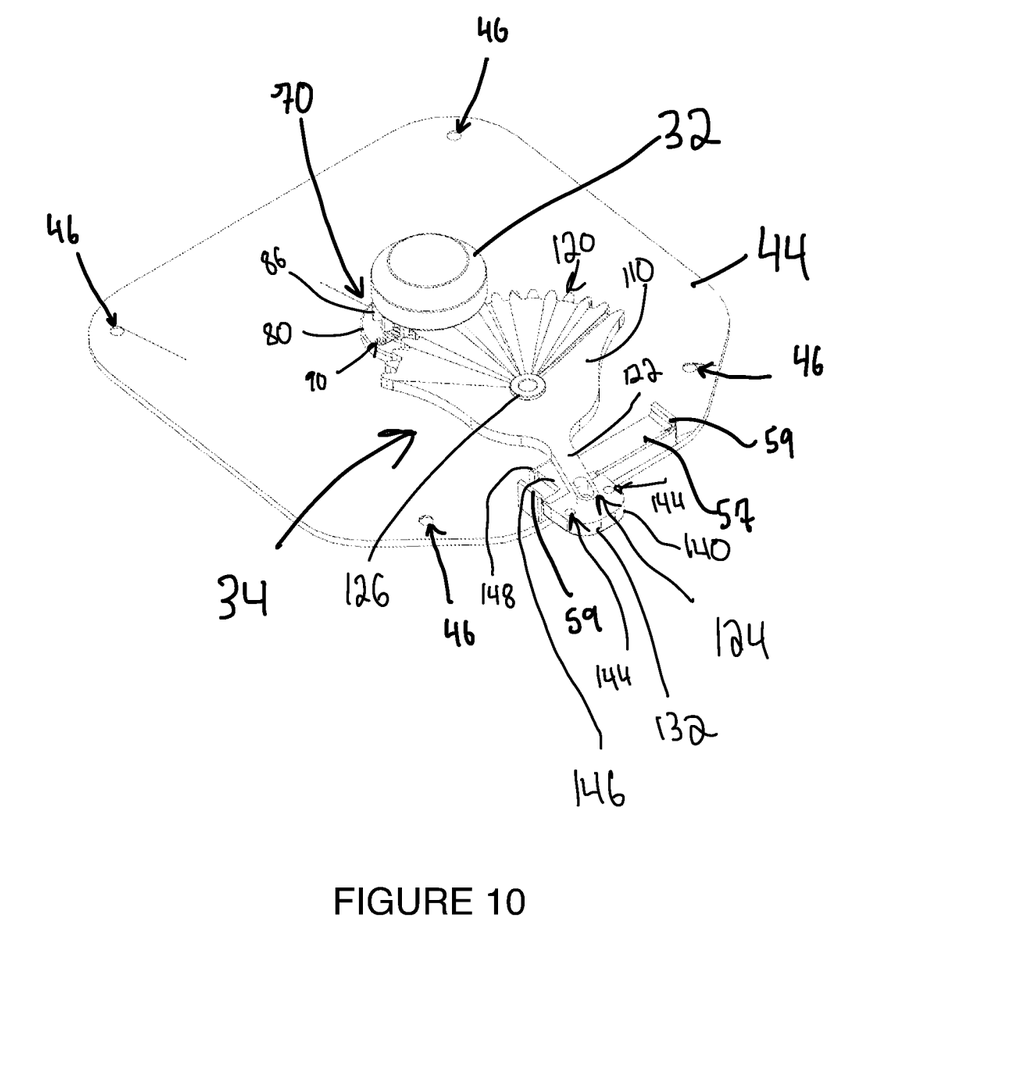
FIG. 10 is a perspective view taken from a top, front, right side of the base member of FIG. 3, with the upper part being omitted.

With reference to FIGS. 9 and 10, the actuation mechanism 34 will now be described in greater detail. The actuation mechanism 34 is positioned at a front of the body 30, and is actuable through the slot 55. The actuation mechanism 34 includes an actuation gear 110 and an actuator 112.

The actuation gear 110 has an arcuate toothed portion 120 that is configured to mesh with the stopper gear 86, and an elongate portion 122 extending opposite to the toothed portion 120. The elongate portion 122, which is configured to at least partially extend through the slot 55 and slide on the guide member 57, defines a channel 124 configured to receive part of the actuator 112 therein. As will be described below, the channel 124 enables the actuator 112 to move along a linear path. Furthermore, the actuation gear 110 is pivotally connected to the body 30 about a pivot point 126. More precisely, the actuation gear 110 is pivotally connected to the upper part 42. In other embodiments, the actuation gear 110 could be pivotally connected to the lower part 44. It is to be noted that the pivot point 126 corresponds to a center of the arcuate tooted portion 120, and is positioned so that the stopper and actuation gears 86, 110 can effectively mesh with one another.

The actuator 112, which is operatively connected to the actuation gear 110, is a lever 112. The lever 112 has an upper portion 130 and a lower portion 132 that are connectable to one another via actuator fasteners (not shown). It is contemplated that in some embodiments, the upper and lower portions 130, 132 could be connected differently, for example by an adhesive. In other embodiments, the upper and lower portions 130, 132 could be one integral piece.

The upper portion 130 has, on a top thereof, two recessed sections 134a, 134b. The recessed sections 134a, 134b assist in providing a better gripping surface to the lever 112. It is contemplated that in some embodiments, the recessed sections 134a, 134b could be omitted, or other features for enhancing grip could be provided. In other embodiments, the upper portion 130 could have a protrusion thereon. On a bottom thereof, the upper portion 130 defines a clearance recess 136. The clearance recess 136 provides clearance for the movement of the elongate portion 122. Extending from the bottom of the upper portion 130, within the clearance recess 136, the upper portion 130 also has a connecting member 138 that is configured to be received in the channel 124. The upper portion 130 also defines two connecting apertures 139 that are laterally spaced. In some embodiments, there could be more or less than two connecting apertures. The connecting apertures 139 are configured to receive the actuator fasteners therein for connecting with the lower part 132.

The lower portion 132 has a base 140 that is generally complementary to the upper portion 130. The base 140 defines two connecting apertures 144 that are laterally spaced. In some embodiments, there could be more or less than two connecting apertures. The connecting apertures 144 are configured to align with the connecting apertures 139, and receive the actuator fasteners therein for connecting with the upper part 130. The lower portion 132 further has, extending rearwardly from the lower portion 132, a sliding element 146 that is configured to slide on the slide member 57. On a rear end of the sliding element 146, there is an anchor 148. The anchor 148 is configured to anchor the actuator 112 to the guide member 57 in the longitudinal direction (i.e., transversally to the guiding member 57), while guiding the movement of the actuator 112 in the lateral direction (i.e., along the guiding member 57).

Figure 3:
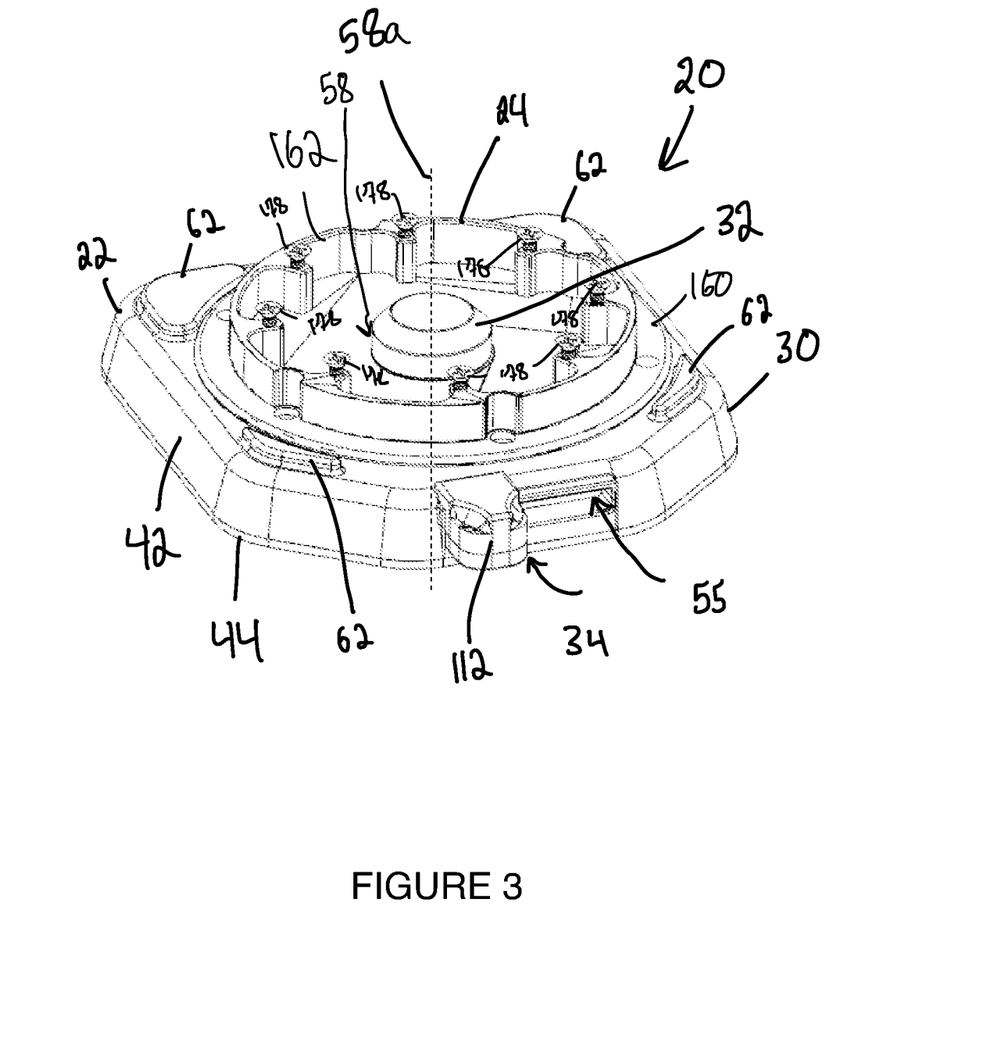
FIG. 3 is a perspective view taken from a top, front, right side of the coupling device of FIG. 1 and a plate member of the holder, with a stopper of a base member of the coupling device being in a neutral position.
Figure 4:
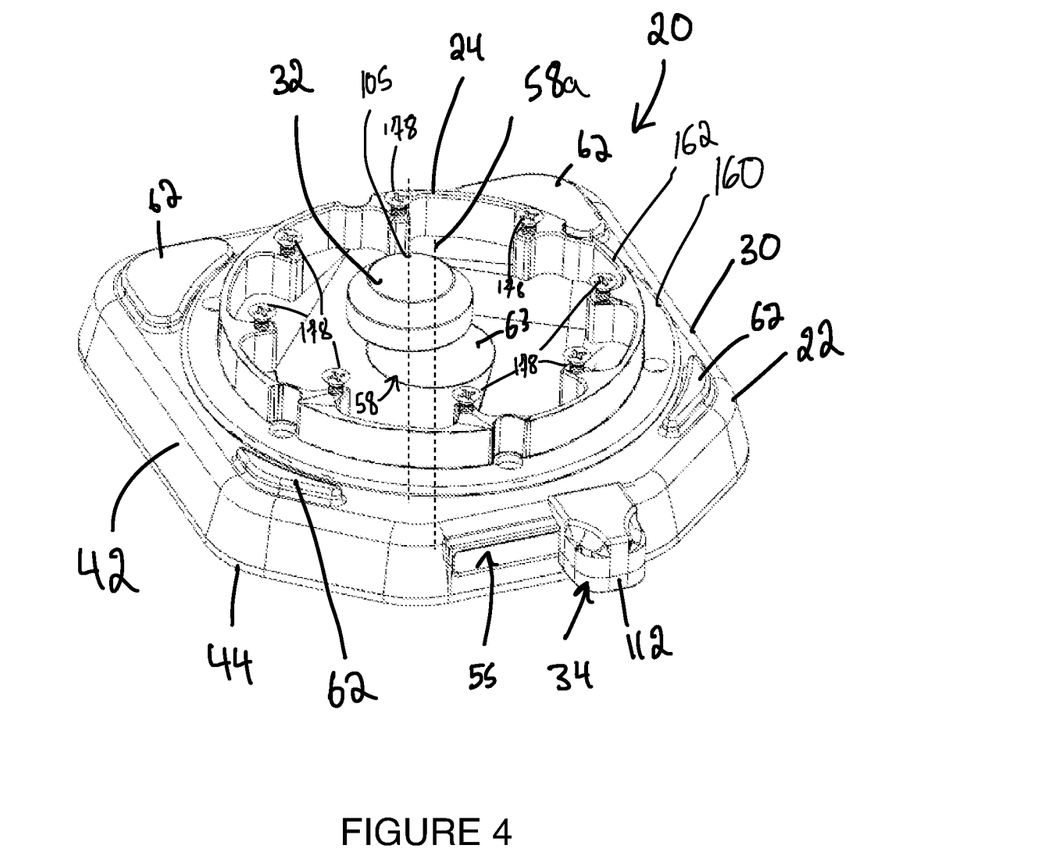
FIG. 4 is a perspective view taken from a top, front, right side of the coupling device of FIG. 1 and a plate member of the holder, with the stopper of the base member of the coupling device being in a locked position.
Figure 5:
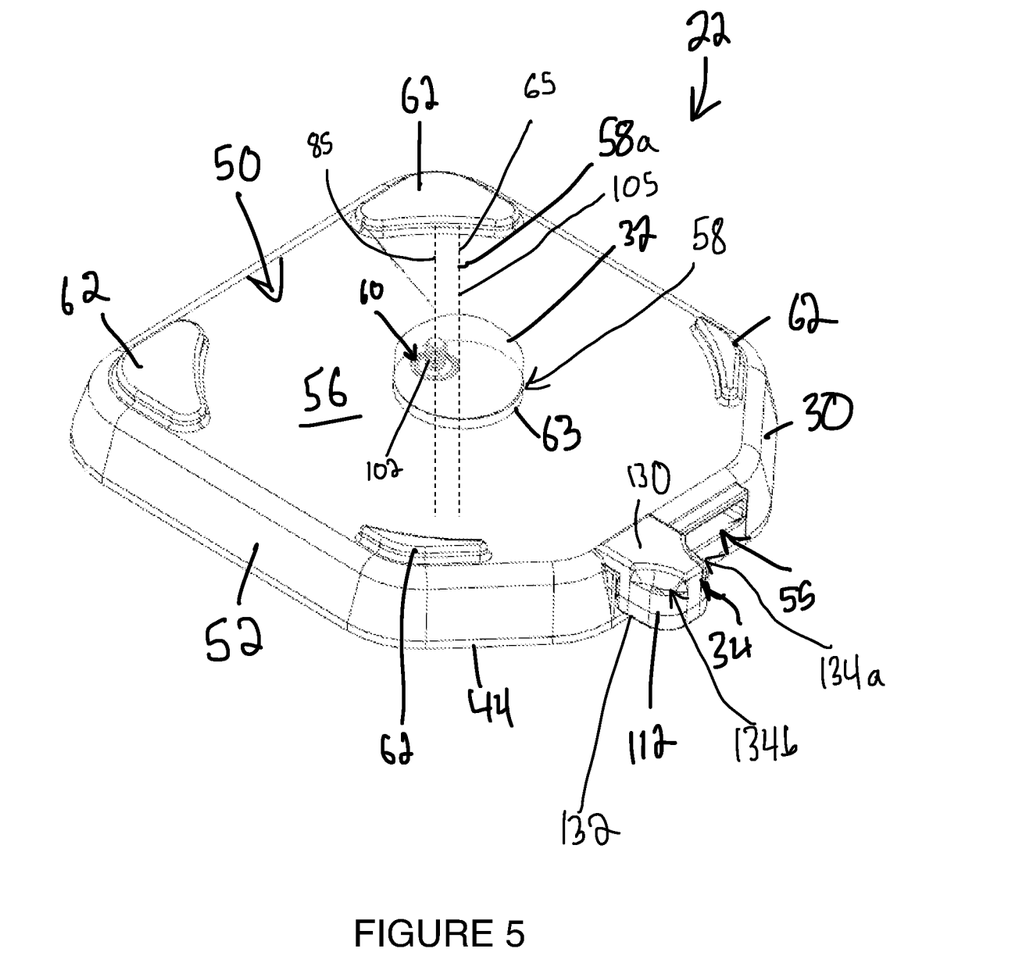
FIG. 5 is a perspective view taken from a top, front, right side of the base member of FIG. 3, with the stopper being in the neutral position.
Figure 6:
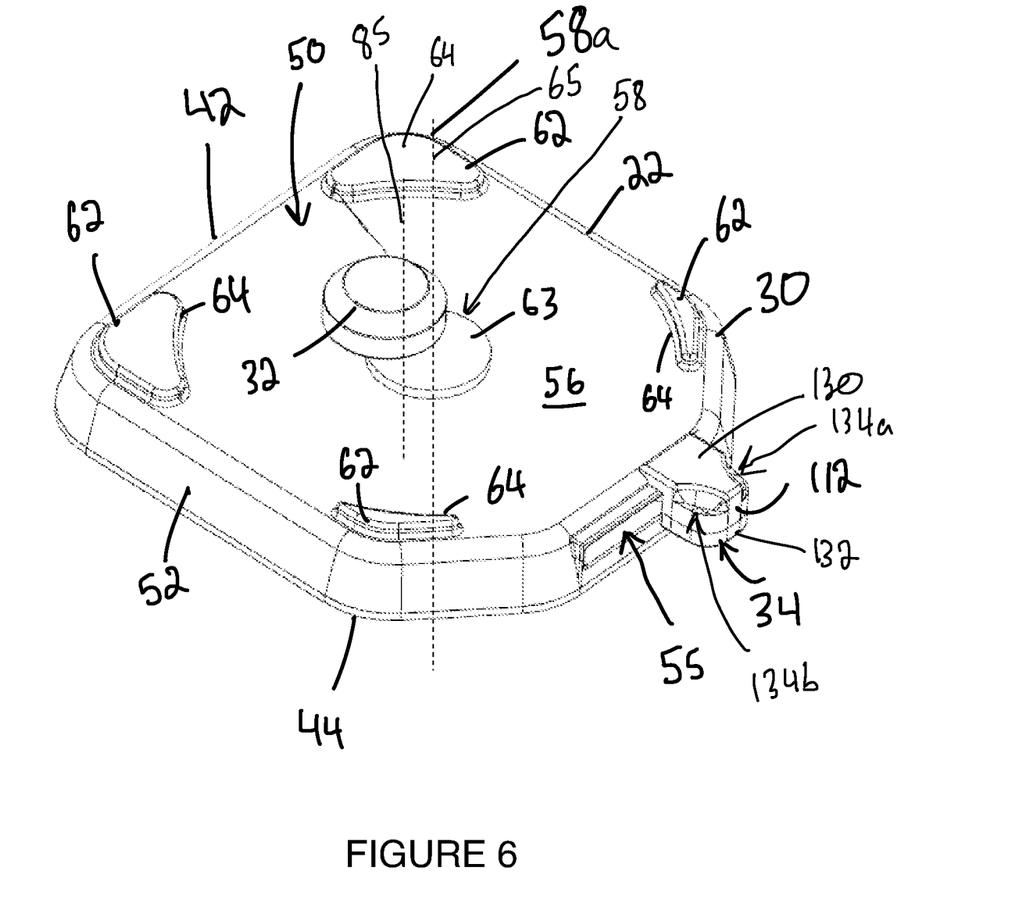
FIG. 6 is a perspective view taken from a top, front, right side of the base member of FIG. 3, with the stopper being in the locked position.
Figure 7:
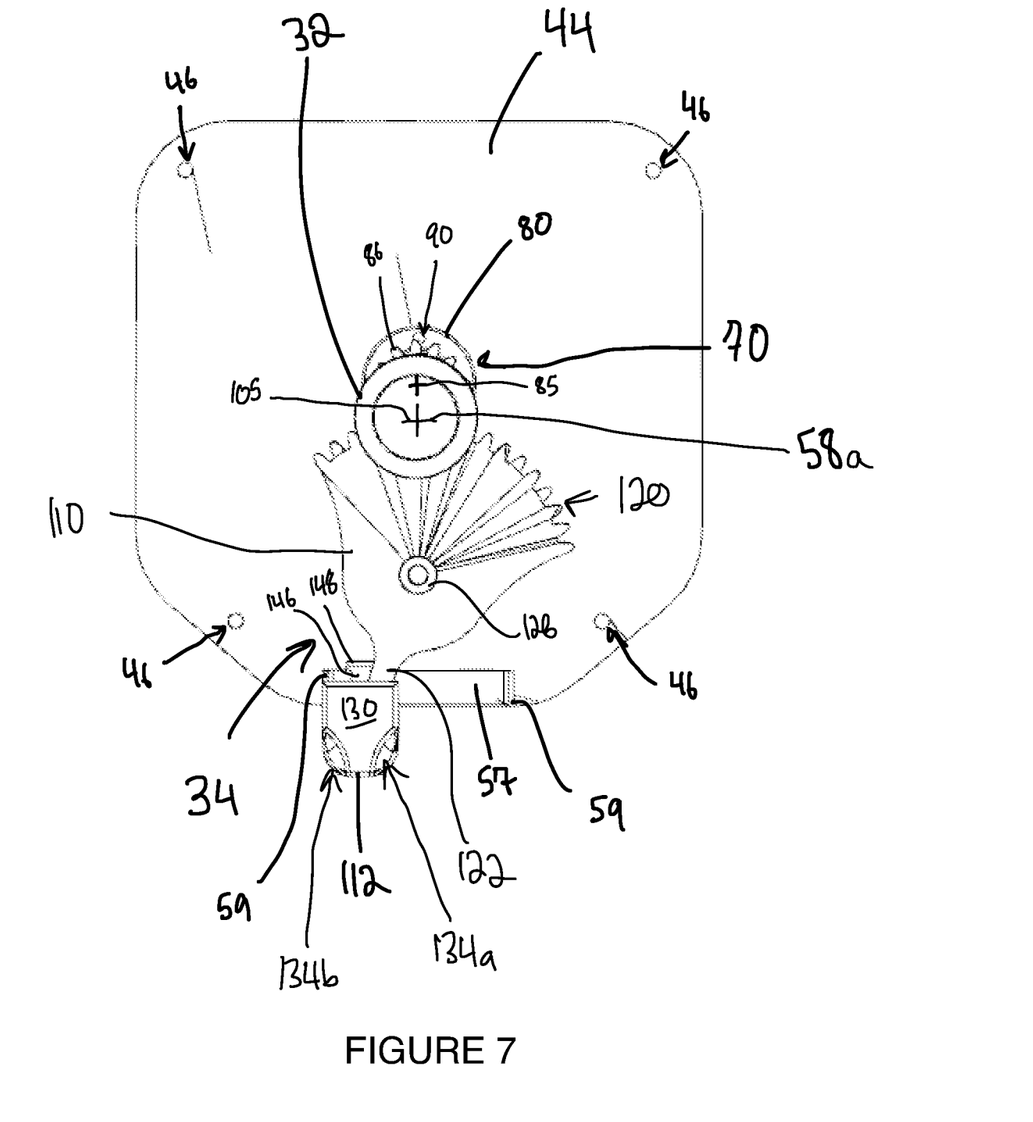
FIG. 7 is a top plan view of the base member of FIG. 3, with an upper part of the base member being omitted.

The actuator 112 is moveable between a neutral actuator position (FIGS. 3 and 5) and a locked actuator position (FIGS. 4 and 6). Movement of the actuator 112 upon reaching the neutral and locked actuator positions is delimited by the stopping segments 59 of the guiding member 57. As mentioned above, the actuator 112 is configured to move along a linear path. This is enabled by the presence of the channel 124 and the clearance recess 136. Indeed, as the actuator 112 moves along its path, the connecting member 138 moves through the channel 124, and the elongate portion 122 moves in the clearance recess 136. It is contemplated that in some embodiments, the actuator 112 could be configured to move along an arcuate path, such that the channel 124 could be omitted.

It is contemplated that in some embodiments, the coupling device 20 could further have a lock for locking the actuation mechanism 34 in at least one of the neutral actuator position and the locked actuator position. For example, in some embodiments, the neck 84 could be resiliently rotationally biased to bias the actuation mechanism 34 toward the locked actuator position. As such, the actuation mechanism 34 would be acting as a release mechanism.

Referring to FIGS. 3, 4 and 11, the plate member 24, which is configured to be selectively connected with the base member 24, will now be described. The plate member 24 has a bottom portion 160 and a sidewall 162 projecting upwardly from the bottom portion 160.

The bottom portion 160 is generally circular. It is contemplated that in other embodiments, the bottom portion 160 could have another shape. The bottom portion 160 has a contact face 170 for contacting the contact face 56. At a center thereof, the bottom portion 160 defines the opening 172 that is configured to receive the stopper 32 therethrough (and part of the central positioning member 63). It is contemplated that in other embodiments, the opening 172 could be offset from a center of the bottom portion 160. As mentioned above, a thickness (i.e., height) of the bottom portion 160 is configured to be received in the gap 106.

The sidewall 162, as mentioned above, extends upwardly from the bottom portion 160. The sidewall 162 has a plurality of ribs 174 extending radially inwardly (i.e., towards the center of the bottom portion 160). Each of the ribs 174 has an aperture 176 configured to receive a plate fastener 178 therein. The plate fasteners are configured to fasten into apertures defined in the holder 23. It is contemplated that in some embodiments, the plate member 24 could be connected to the holder 23 differently. The holder 23 will not be described herewith. It is contemplated that in some embodiments, the holder 23 could differ from one embodiment to another, depending on the device 21 that is to be connected to the coupling device 20. The holder 23 may be omitted and the plate fasteners could be connected directly to the device.

A description of the device 21 being connected to the coupling device 20 will now be provided. Specifically, a description of the plate member 24 being connected to the base member 22 will now be provided.

Initially, as shown in FIG. 3 the stopper 32 is in the neutral position. As such, the stopper 32 is aligned within the alignment area 58 and a center of the stopper is aligned with the center of the alignment area 58. This configuration of the base member 22 enables the plate member 24 to connect to the base member 22.

Then, referring to FIGS. 1 to 3, the device 21, and thus the holder 23 and the plate member 24, is connected to the base member 22. To do so, the plate member 24 is positioned so that the opening 172 is aligned with the stopper 32 (and thus the opening 172 is aligned with the alignment point 58), before being lowered until the contact face 170 of the bottom portion 160 contacts the contact portion 56. It is to be noted that the opening 172 does not have be exactly aligned with the stopper 32, as the peripheral and central positioning members 62, 63 assist in positioning the plate member 24 relative to the base member 22. Specifically, the peripheral positioning members 62 abut with the outer radial surface of the bottom portion 160, and the central positioning member 63 is partially received in the opening 170. Upon connection, the coupling device 20 is in the connected mode. In this configuration, the plate member 24 can be selectively disconnected from the base member 22. In other words, movement of the plate member 24 relative to the base member 22 away from one another is not restricted.

Referring to FIGS. 4 and 6, the actuation mechanism 34 is then actuated to move the stopper 32 to the locked position. Specifically, the actuator 112 is moved from the neutral actuator position to the locked actuator position. In some embodiments, this can be done by manipulating the actuator 112 thanks to the recessed sections 134a, 134b. Due to the operative connection between the actuator 112 and the actuation gear 110, in response to the actuator 112 being moved from the neutral actuator position to the locked actuator position, the actuation gear 110 pivots about the pivot point 126. Thus, the elongate portion 122, which is a portion of the actuation gear 110, pivots, and moves about an arcuate path. Due to the clearance recess 136, the end of the elongate portion 122 received in the actuator 112 does not abut the actuator 112. Instead, the connecting member 138 moves along the channel 124 as the actuator 112 moves toward the locked actuator position.

Since the actuation gear 110 operationally engages the stopper gear 86, the pivotal motion of the actuation gear 110 causes the stopper gear 86 to rotate. Specifically, the stopper gear 86 rotates about the central neck axis 85. Given that the stopper gear 86 is fixedly connected to the neck 84, rotation of the stopper gear 86 causes the neck 84 to also rotate about the central neck axis 85. The neck 84 rotates relative to the upper and lower retainers 82a, 82b because of, as mentioned above, the low friction therebetween.

Rotation of the neck 84 causes the stopper 32 to move to the locked position. Since the neck 84 is offset from the central stopper axis 105, the stopper 32 moves (rather than rotating in place). In the locked position, the stopper 32 extends over a part of the lower portion 160 so as to restrict movement of the plate member 24 away from the base member 22. It is to be noted that the stopper 32 can slide over the plate member 24 without abutting it due to the presence of the gap 106 and the selected thickness of the plate member 24.

When the stopper 32 is in the locked position, the movement of the plate member 24 away from the base member 22 is restricted due to the engagement of various members of the connecting assembly 70 and the body 30. For example, with reference to FIG. 8, if it is attempted to disconnect the plate member 24 from the base member 22 (i.e., moving the plate member 24 transversely away from the base member 22), the plate member 24 abuts the stopper 32. The stopper 32, however, generally does not move, since the stopper 32 is fixedly connected to the neck 34, which in turn, abuts the retainer 82b, which itself abuts the body 30. In more detail, as the stopper 32 tries to move in an upward direction, the neck 84 also attempts to move in the upward direction. The intermediate portion 100 then abuts the lower surface of the flange 96 of the upper retainer 82b, and the upper surface of the flange 96 abuts a lower surface of the upper part 42 of the body 30. The upper surface of the flange 96 abuts the lower surface of the upper part 42, because the flange 96 is wider than the stopper aperture 60.

It is to be noted that due to the configuration of the base and plate members 22, 24, notably the circular configuration of the bottom portion 160, when the coupling device 20 is in the connected mode, regardless of whether the stopper 32 is in the neutral or locked positions, the plate member 22, and thus the device 21, is free to rotate relative to base member 22 about the alignment point 58. In some embodiments, this relationship is assisted by there being low friction between the base and plate members 22, 24. This enables a user to adjust a position of the device 21 without having to disconnect the device 21 from the base member 22.

Then, to disconnect the device 21, and thus the holder 23 and the plate member 24, from the base member 22, the actuation mechanism 34 is actuated to move the actuator 112 toward the neutral actuator position, thereby causing the stopper 32 to move back toward the neutral position. Since the stopper 32 does not extend over part of the plate member 22, the plate member 22, the holder 23 and the device 21, can be moved away from the base member 22. After being removed, the coupling device 20 is in the disconnected mode.

It is to be noted, as mentioned above, that the support surface to which the base member 22 is connected can be a vertically or horizontally extending support surface. In embodiments where the support surface extends vertically (e.g., a wall), the device 21, and thus the holder 23 and the plate member 24, must be held in position relative to the base member 22 (i.e., maintained in the connected mode) until the stopper 32 is moved to the locked position.

Modifications and improvements to the above-described embodiments of the present invention may become apparent to those skilled in the art. The foregoing description is intended to be exemplary rather than limiting. The scope of the present invention is therefore intended to be limited solely by the appended claims.

What is claimed is:

1. A coupling device comprising a base member and a plate member, the base and plate members being configured to be releasably connectable to one another;
   the base member having:
      a body with a coupling face having a contact portion for contacting a contact face of the plate member in a connected mode of the coupling device, the contact portion including an alignment area which corresponds to a position of an opening of the plate member when the coupling device is in the connected mode;
      a stopper operatively connected to the body, and extending from the coupling face and positioned in the contact portion, the stopper being sized and shaped to be received in the opening of the plate member, the stopper being moveable between:
         a neutral position in which the stopper is aligned with the alignment area and can be received in the opening of the plate member when the coupling device is in the connected mode, the neutral position of the stopper permitting removal of the plate member from the base member, and
         a locked position in which the stopper is misaligned with the alignment area, and when the contact face of the plate member contacts the contact area with the stopper received in the opening, the stopper extends over a part of the plate member to restrict movement of the plate member away from the base member; and
      an actuation mechanism for selectively moving the stopper between the neutral and locked positions.

2. The coupling device of claim 1, wherein in the neutral position, a central axis of the stopper is aligned with the central axis of the alignment area of the contact portion.

3. The coupling device of claim 1, wherein the stopper is connected to the actuation mechanism by a neck extending away from the coupling face, a thickness of the stopper being greater than a thickness of the neck.

4. The coupling device of claim 3, wherein the stopper is asymmetrically attached to the neck such that a central axis of the neck is misaligned with a central axis of the stopper.

5. The coupling device of claim 4, wherein the actuation mechanism is configured to rotate the neck about the central axis of the neck, the rotation of the neck causing the movement of the stopper between the neutral and locked positions.

6. The coupling device of claim 3, wherein the actuation mechanism comprises an actuator connected to the neck by one or more gears, for effecting rotation of the neck on actuation of the actuator.

7. The coupling device of claim 6, wherein the actuator is a lever.

8. The coupling device of claim 7, further comprising a guide member on the base member, the lever being configured to slide along the guide member.

9. The coupling device of claim 7, wherein the one or more gears comprise:
   a first gear, which is a gear wheel, extending around, and attached to, the neck, and
   a second gear pivotally connected to the body of the base member about a pivot point, the second gear having a first portion attached to the actuator and a second portion engaged with the first gear wheel, and the second gear pivoting on actuation of the actuator.

10. The coupling device of claim 1, wherein the stopper is spaced from the coupling face, thereby defining a gap sized to accommodate a thickness of the plate member.

11. The coupling device of claim 1, further comprising at least one positioning member on the coupling face of the base member for defining at least a portion of a perimeter of the contact portion and delimiting a movement of the plate member along the coupling face.

12. The coupling device of claim 11, wherein the at least one positioning member comprises at least one protrusion extending from the contact portion.

13. The coupling device of claim 1, further comprising a lock for locking the actuation mechanism in one of the neutral and locked positions.

* * * * *